United States Patent [19]

Wolf

[11] 4,092,353

[45] May 30, 1978

[54] PROCESS FOR THE PURIFICATION OF BENZOIC ACID

[75] Inventor: Wilhelm Wolf, Krefeld, Germany

[73] Assignee: Bayer Aktiengesellschaft, Leverkusen, Germany

[21] Appl. No.: 820,516

[22] Filed: Jul. 29, 1977

[30] Foreign Application Priority Data

Aug. 13, 1976  Germany .......................... 2636489

[51] Int. Cl.² ............................................. C07C 51/42
[52] U.S. Cl. ................................................... 260/525
[58] Field of Search ........................... 260/525, 524 R

[56] References Cited

U.S. PATENT DOCUMENTS 1,822,016  9/1931  Daniels ................................. 260/525
3,235,588  2/1966  Weaver ................................. 260/525

Primary Examiner—A. Siegel
Attorney, Agent, or Firm—Burgess, Dinklage & Sprung

[57] ABSTRACT

A process for purifying benzoic acid, especially benzoic acid obtained by the catalytic oxidation of toluene in the liquid phase which can be contaminated with impurities such as diphenyl, methyldiphenyl, a phenyl-benzoic acid, benzaldehyde, benzyl benzoate, succinic anhydride, phthalic anhydride, formic acid or formaldehyde, by contacting the benzoic acid with an amine of the formula $H_2N - R$ 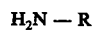

wherein R is hydrogen, a straight or branched chain alkyl radical of 1 to 4 carbon atoms or a cycloalkyl radical of 5 or 6 carbon atoms or a salt thereof and benzoic acid is distilled off or sublimed from the resultant reaction mixture. The benzoic acid so obtained can be reacted with sodium hydroxide solution and highly pure sodium benzoate can be removed by extraction with toluene or steam distillation.

7 Claims, No Drawings

PROCESS FOR THE PURIFICATION OF BENZOIC ACID

The invention relates to a process for the preparation of pure sodium benzoate.

According to the Deutsches Arzneibuch (German Pharmacopeia) (DAB VII, 689–691 (1968)), sodium benzoate should be a white, finely crystalline or granular powder with a peculiar sweetish or salty taste. Criteria mentioned are, inter alia, the solublity in 90% pure ethanol to give a clear solution, the proportion of impurities and its behaviour towards sulphuric acid. The requirements in other pharmacopeia (U.S. Pharmacopeia 17, British Pharmacopeia 63, Schweizer Pharmakopoe (Swiss Pharmacopeia) and Japanese Pharmacopeia) essentially correspond to the requirements in the Deutsches Arzneibuch (German Pharmacopeia).

It is known to purify benzoic acid to remove contaminants, such as phthalic acid, by subliming technical grade benzoic acid in the presence of glycerol and castor oil (Chemisches Zentralblatt 1942, II, page 2,642).

SUMMARY OF THE INVENTION

In accordance with the present invention there is provided an improved process for purifying benzoic acid such as benzoic acid resulting from the catalytic oxidation of toluene in the liquid phase. The benzoic acid so obtained can be converted into sodium benzoate of high purity simply by contacting the benzoic acid with a sodium hydroxide solution and extracting or steam distilling sodium benzoate from the resultant reaction mixture. In accordance with the present invention benzoic acid contaminated with impurities is purified by contacting the same with a small amount of an amine of the formula $$H_2N - R$$

wherein R is hydrogen, a straight-chain or branched alkyl radical having 1 to 4 carbon atoms in the chain or a cycloalkyl radical having 5 to 6 carbocyclic carbon atoms, or a salt thereof, at an elevated temperature and distilling or subliming benzoic acid from the resultant reaction mixture.

The benzoic acid can be removed from the amine-impure benzoic acid reaction mixture while amine is contacting the contaminated benzoic acid or it can be removed subsequently. The benzoic acid can be distilled or sublimed from the reaction mixture in a manner which is itself known. Following removal of the benzoic acid from the reaction mixture, the benzoic acid can be recovered or, alternatively, it can be reacted with a sodium hydroxide solution in a known manner to prepare sodium benzoate. The sodium benzoate can be removed from the resulting reaction mixture by extraction with toluene and/or steam distillation.

The preparation of benzoic acid by catalytic oxidation of toluene in the liquid phase can be carried out in a generally customary manner (Ullmann's Enzyklopedie der Technischen Chemie (Ullmann's Encyclopaedia of Industrial Chemistry), 4th edition, volume 8, pages 367 – 369 (1974)). Oxidation with atmospheric oxygen can be carried out in the presence of metal compounds as catalysts, for example cobalt compounds and manganese compounds, and of promoters, for example hydrogen bromide or compounds which split off hydrogen bromide.

In general, a benzoic acid which is obtained after distilling off the excess toluene is employed for the treatment, according to the invention, of the benzoic acid with an amine or ammonium salt. It is also possible to use a benzoic acid which has already been distilled or sublimed.

However, it is advantageous to employ benzoic acid in the form in which it is obtained after the oxidation and distillation of the toluene.

In general, the benzoic acid which is obtained after oxidation of toluene is impure. Possible impurities are essentially by-products which have formed during the oxidation or were contained in the starting compounds. Examples of impurities which may be mentioned are diphenyl, methyldiphenyl, phenyl-benzoic acids, benzaldehyde, benzyl benzoate, succinic anhydride, phthalic anhydride, formic acid and formaldehyde.

The proportion of impurities in the benzoic acid after the oxidation is generally not greater than 10% and preferably 8%.

Examples which may be mentioned of amines which, for reasons of expediency or cost, can be employed for the process according to the invention are ammonia, methylamine, ethylamine, propylamine, iso-propylamine, butylamine, iso-butylamine, cyclopentylamine and cyclohexylamine, preferably ammonia.

It is, of course, possible to use all of the possible salts of the amines for the process according to the invention. For carrying out the process industrially, however, it can be appropriate to employ those salts which do not produce any corrosive by-products when they are decomposed. Examples of salts which may be mentioned are the carbonates, bicarbonates, acetates, oxylates and benzoates, preferably the bicarbonates, of the above-mentioned amines.

It is, of course, also possible to employ mixtures of the amines and/or their salts for the process according to the invention.

Small amounts of amines and/or ammonium salts suffice for the process according to the invention. The amount required in a particular case depends on the benzoic acid formed from the oxidation of toluene and can easily be determined by known analytical methods. In general, however, it suffices when the amine and/or the ammonium salt is employed in amounts of 0.004 to 0.01, and preferably 0.005 to 0.006, mol, relative to 1 mol of benzoic acid.

However, for the process according to the invention it is not significant if an excess of the amine or of the ammonium salt is employed. This can be an advantage if individual analyses are to be saved in a batch-wise procedure.

The process according to the invention can be carried out in the temperature range between about 100° C and the boiling point of benzoic acid. In general, the process according to the invention is carried out in the temperature range of 100°–250° C, preferably of 115°–230° C and particularly preferentially of 130°–180° C.

Pure sodium benzoate which can be prepared by the process according to the invention meets the requirements of the pharmacopeias.

The process according to the invention can, for example, be carried out as follows:

After the catalytic oxidation of toluene with atmospheric oxygen, the excess toluene is distilled off. The benzoic acid which is thus obtained is mixed well with an amine and/or an ammonium salt at the chosen reaction temperature. The purified benzoic acid is distilled or sublimed, either already during the treatment, according to the invention, with the amine and/or the ammonium salt or subsequently.

Appropriately, ammonia or the primary amine can be added by passing the gases into, or by adding the aqueous solutions to, the molten liquid benzoic acid at appropriate temperatures, that is to say above its melting point, whilst mixing well.

In a particular embodiment of the process according to the invention, a concentrated aqueous ammonia (ammonium hydroxide) solution, preferably with an ammonia content of 15 - 25%, is mixed with the benzoic acid at a temperature above the melting point of the benzoic acid and preferably in the temperature range of 150°-190° C.

It is also possible to mix solid benzoic acid with the amine, and preferably with aqueous solutions of the amine, at room temperature or temperatures up to the melting point of the benzoic acid. In this case, however, care must be taken that the amine is present in the mixture in a sufficient amount and does not escape on warming before the start of the treatment.

The ammonium salts can also be mixed into the molten liquid benzoic acid. Advantageously, they are mixed with the benzoic acid before warming.

The distillation and/or sublimation of the benzoic acid can be carried out in a manner which is in itself known (Ullmann's Encyklopaedie der techn. Chemie (Ullmann's Encyclopaedia of Industrial Chemistry), 4th edition, volume 8, pp 366-382 (1974)).

According to a particular variant of the process according to the invention the procedure can be, for example, as follows:

Gaseous ammonia or aqueous ammonia solution is mixed continuously, at about 150°-200° C and preferably at 170°-195° C, whilst stirring, into the hot liquid crude benzoic acid which is obtained from a continuous oxidation of toluene and toluene distillation and is in the collection vessel.

This crude benzoic acid mixed with ammonia can follow then be distilled discontinuously or continuously under normal pressure or under reduced pressure, especially under between 25 and 30 mbars.

The benzoic acid obtained after the distillation or sublimation can be reacted with aqueous sodium hydroxide solution in a manner which is in itself known to give sodium benzoate.

The residues of diphenyl can largely be removed in a manner which is in itself known by extraction with toluene and/or by steam distillation (Ullmann, Encyklopadie der technischen Chemie (Encyclopaedia of Industrial Chemistry), 4th edition, volume 8, page 368 (1974)). The sodium benzoate can then be isolated from the aqueous solution, for example by evaporation or spray crystallisation or with the aid of drying drums.

The process according to the invention advantageously makes it possible in a simple manner to prepare a sodium benzoate which meets the requirements of the pharmacopeias. The process can advantageously be carried out on an industrial scale. The formation of resins, which arise in the case of the known sublimation in the presence of glycerol and castor oil, does not take place.

Since it is known that benzoic acid and aqueous ammonia already form benzamide at room temperature (Mh. Chemie 27, 34 (1906)), it is surprising that the treatment according to the invention can be carried out with only small amounts of the amine and that hardly any reaction products of a different type are formed. As is known, benzamide is also formed when ammonium benzoate is heated (J. prakt. Chem. (2) 29, 431 (1884)). It is also known that benzonitrile is formed in a melt of ammonium benzoate (Liebig's Ann. Chem. 208, 291 (1881)).

Sodium benzoate which corresponds to the requirements of the pharmacopeias can be used as a preservative for foodstuffs (Romps Chemielexikon (Romps Chemical Dictionary), 7th edition, volume 4, page 2,268, Chemiker-Ztg. 32, 950, C. 1908 II, 1882 and Chemiker-Ztg. 33, 181).

The benzoic acid employed in the examples which follow is prepared by atmospheric oxidation of toluene in the presence of cobalt compounds at temperatures of 160° to 180° C. After the reaction, the toluene is distilled off from the reaction mixture, first at a sump temperature of 175° to 190° C and under a pressure of 1010 mbars and finally at a sump temperature of 190° C and under a pressure of 100 mbars:

EXAMPLE 1

500 g of benzoic acid are mixed with 2.5 g of ammonium bicarbonate and then distilled in vacuo through a column (20 theoretical plates) using a reflux ratio of 1 : 1. The distillate (490 g) which is obtained at a temperature at the top of 146° C/25 mbars is converted to sodium benzoate by adding 10% strength by weight sodium hydroxide solution until the aqueous solution has a pH value of 7.0. Residues of diphenyl and similar compounds are removed with the aid of a steam distillation. This solution is then evaporated and the residue is dried.

The sodium benzoate thus obtained dissolved in 54 parts by weight of ethyl alcohol with a density of 0.828 at 20° C to give a clear solution. It meets the requirements of the sulphuric acid test according to Deutsches Arzneibuch (German Pharmacopeia) (DAB VII, 689-691 (1968)

EXAMPLE 2

0.6 g of gaseous ammonia is passed into 500 g of benzoic acid at 150° C and the resulting mixture is then distilled as described in Example 1.

The resulting distillate is introduced into 1,100 ml of 11.7% strength by weight aqueous sodium hydroxide solution and the aqueous solution is neutralised to a pH of 7.0 by adding a further 113 ml of 11.7% strength by weight aqueous sodium hydroxide solution. Residues of diphenyl and similar compounds are removed with the aid of a steam distillation. Evaporation of the aqueous solution gives 578 g of sodium benzoate. The sodium benzoate thus obtained dissolves in 54 parts by weight of ethyl alcohol with a density of 0.828 at 20° C to give a clear solution and meets the requirements of the sulphuric acid test according to Deutsches Arzneibuch (German Pharmacopeia) (DAB VII, 689-691 (1968).

EXAMPLE 3

500 g of benzoic acid are mixed with 5 g of ammonium benzoate, the mixture is heated to 150° C and the benzoic acid is sublimed whilst passing nitrogen through the mixture and cooling the benzoic acid vapour/nitrogen mixture.

488 g of a sublimed benzoic acid are obtained and this is reacted with sodium hydroxide solution to give sodium benzoate. Residues of diphenyl and similar compounds are removed with the aid of a steam distillation.

The aqueous solution is evaporated and the residue is dried.

The resulting sodium benzoate also dissolves in ethyl alcohol with a density of 0.828 at 20° C to give a clear solution and meets the requirements of the sulphuric acid test according to Deutsches Arzneibuch (German Pharmacopeia) (DAB VII, 689–691 (1968).

EXAMPLE 4

500 g of benzoic acid are mixed, at 150° C, with 1.0 g of cyclohexylamine and distilled in vacuo in a column (20 theoretical plates) using a reflux ratio of 1 : 1. The distillate (491 g) which is obtained at a temperature at the top of 146° C/25 mbars is subsequently dissolved in about 1,100 ml of 11.7% strength by weight aqueous sodium hydroxide solution and the aqueous solution is neutralised to a pH value of 7.0 by adding further 11.7% strength by weight aqueous sodium hydroxide solution.

In order to remove unconverted excess cyclohexylamine, about 200 g of water are then distilled off from the solution. Residues of diphenyl and similar compounds are removed with the aid of a steam distillation. The solution is then evaporated and the residue is dried. The resulting sodium benzoate dissolves in ethyl alcohol to give a clear solution, as described, and meets the requirements of the sulphuric acid test according to Deutsches Arzneibuch (German Pharmacopeia) (DAB VII, 689–691 (1968).

EXAMPLE 5

1.67 g of methylamine (4.4 ml of an aqueous solution containing 385 g/l) were added to 761 g of benzoic acid, the mixture was heated briefly to 150° C and the benzoic acid was distilled as described in Example 1. Residues of diphenyl and similar compounds are removed with the aid of a steam distillation. 750 g of distillate were obtained and are converted, as described in Example 1, to sodium benzoate.

As described above, the resulting sodium benzoate dissolves in ethyl alcohol to give a clear solution and meets the requirements of the sulphuric acid test according to Deutsches Arzneibuch (German Pharmacopeia) (DAB VII, 689–691 (1968).

EXAMPLE 6

In a stirred vessel which holds 5 tonnes of benzoic acid, 5.2 l of 25% strength by weight aqueous ammonia solution are added per hour, at 150° to 190° C, through an inlet tube in the base of the vessel to 1,350 kg of benzoic acid, which are obtained per hour, in the manner described above, from an industrial plant for the oxidation of toluene, after distilling off the toluene, and the two compounds are mixed by stirring.

The benzoic acid mixed with ammonia in this way is then distilled under a pressure of 25 mbars through a packed column with 35 theoretical plates.

The pure benzoic acid obtained as the distillate is converted into an aqueous solution of sodium benzoate using, per 100 kg of distillate, 27.73 kg of sodium hydroxide in the form of an approximately 11.7% strength by weight aqueous solution of sodium hydroxide, by dissolving the distillate in less than the calculated amount of sodium hydroxide solution and then adding further sodium hydroxide solution until the pH value is 7.0 (about 230 kg); this solution is extracted with toluene in a ratio of 50:1 (solution:toluene) in 5 stages. Residues of diphenyl and similar compounds are removed with the aid of a steam distillation. About 40 kg of water are then distilled off and the residual solution is evaporated over drying drums at 160° C. The resulting sodium benzoate dissolves in ethyl alcohol to give a clear solution, in the manner described above.

The sodium benzoate prepared in Example 6 meets the requirements of Deutsches Arzneibuch (German Pharmacopeia) (DAB VII, 689–691 (1968)) with regard to purity.

What is claimed is:

1. A process for purifying benzoic acid which comprises contacting benzoic acid with an amine of the formula

$$H_2N - R$$

wherein
R is hydrogen, a straight or branched chain alkyl radical of 1 to 4 carbon atoms or a cycloalkyl radical with 5 to 6 carbon atoms or a salt thereof in an amount of 0.004 to 0.01 mol per mol of benzoic acid at a temperature of 100° C to 250° C and distilling over or subliming benzoic acid from the resultant mixture.

2. A process according to claim 1 wherein the benzoic acid is contaminated with an impurity selected from the group consisting of diphenyl, methyldiphenyl-,aphenyl-benzoic acid, benzaldehyde, benzyl benzoate, succinic anhydride, phthalic anhydride, formic acid and formaldehyde.

3. A process according to claim 1 wherein ammonia is employed as the amine..

4. A process according to claim 1 wherein the amine is in the form of a salt and said salt is ammonium bicarbonate.

5. A process according to claim 1 wherein the benzoic acid is treated with a 15 to 25% by weight aqueous ammonium hydroxide solution at a temperature in the range of 150° to 190° C.

6. A process according to claim 1 wherein benzoic acid is formed by the catalytic oxidation of toluene in the liquid phase.

7. A process according to claim 1 wherein the purified benzoic acid removed by distillation or sublimation is contacted with a sodium hydroxide solution and sodium benzoate is extracted from the resultant reaction mixture with toluene or the reaction mixture is subjected to a steam distillation.

* * * * *